(12) United States Patent
DeNardo et al.

(10) Patent No.: US 7,029,652 B2
(45) Date of Patent: Apr. 18, 2006

(54) METHOD OF TREATING TUMORS

(75) Inventors: Sally J. DeNardo, El Macerco, CA (US); Patricia A. Burke, Sacramento, CA (US); Gerald L. DeNardo, El Macerco, CA (US); Simon Goodman, Darmstadt (DE); Siegfried Matzku, deceased, late of Zwingenberg (DE); by Kerstin Matzku, legal representative, Zwingenberg (DE)

(73) Assignees: The Regents of the University of California, Oakland, CA (US); Merck Patent GmbH, Darmstadt (DE)

( * ) Notice: Subject to any disclaimer, the term of this patent is extended or adjusted under 35 U.S.C. 154(b) by 240 days.

(21) Appl. No.: 10/208,931

(22) Filed: Jul. 31, 2002

(65) Prior Publication Data

US 2003/0143157 A1 Jul. 31, 2003

Related U.S. Application Data

(63) Continuation-in-part of application No. 09/787,374, filed as application No. PCT/EP99/06654 on Sep. 9, 1999, now Pat. No. 6,683,051.

(30) Foreign Application Priority Data

Sep. 16, 1998 (DE) ................................ 198 42 415

(51) Int. Cl.
*A61K 51/00* (2006.01)
(52) U.S. Cl. ..................... 424/1.49; 424/133.1; 514/17
(58) Field of Classification Search .................... 514/1, 514/9; 435/6, 7; 530/300
See application file for complete search history.

(56) References Cited

OTHER PUBLICATIONS

Burke PA, DeNardo SJ, Miers LA, Kukis DL, DeNardo GL., Combined modality radioimmunotherapy. Promise and peril.Cance Feb. 15, 2002;94(4 Suppl):1320-31.*
DeNardo et al., Neovascular targeting with cyclic RGD peptide (cRGDf-ACHA) to enhance delivery of radioimmunotherapy. Cancer Biother Radiopharm. Feb. 2000;15(1): 71-9.*
Lode et al., Synergy between an antiangiogenic integrin alphav antagonist and an antibody-cytokine fusion protein eradicates spontaneous tumor metastases. Proc Natl Acad Sci U S A. Feb. 16, 1999;96(4):1591-6.*

* cited by examiner

*Primary Examiner*—Robert A. Wax
*Assistant Examiner*—Shawn A. Hamidinia
(74) *Attorney, Agent, or Firm*—Olson & Hierl, Ltd.

(57) ABSTRACT

A method of treating tumors, such as prostate tumors, breast tumors, non-Hodgkin's lymphoma, and the like, includes the sequential steps of administering to the patient at least one dose of an antiangiogenic cyclo-arginine-glycine-aspartic acid-containing pentapeptide (cRGD pentapeptide); administering to the patient an anti-tumor effective amount of a radioimmunotherapeutic agent (RIT); and then administering to the patient at least one additional dose of cRGD pentapeptide. The cRGD pentapeptide is preferably cyclo-(Arg-Gly-Asp-D-Phe-[N-Me]-Val), and the RIT is preferably a radionuclide-labeled chelating agent-ligand complex in which chelating agent is chemically bonded to a tumor-targeting molecule, such as a monoclonal antibody.

33 Claims, 6 Drawing Sheets

METHOD OF TREATING TUMORS

CROSS-REFERENCE TO RELATED APPLICATIONS

This application is a continuation-in-part of U.S. patent application Ser. No. 09/787,374, filed on Jun. 4, 2001 now U.S. Pat. No. 6,683,051 which is a 371 of PCT/EP99/06654 filed Sep. 9, 1999.

STATEMENT OF GOVERNMENT INTEREST

A portion of the work described herein was supported by grant number PO1 CA-47829 from the National Cancer Institute, and by grants number DEFG01-00NE22944 and DEFG03-84ER60233 from the United States Department of Energy. The United States Government may retain certain rights in this invention.

FIELD OF THE INVENTION

The invention relates to methods of treating tumors. More particularly the invention relates to treatment of tumors with a combination of radioimmunotherapy and an integrin receptor antagonist.

BACKGROUND OF THE INVENTION

Novel and synergistic therapeutic combinations are desirable for the treatment of metastatic breast cancer, prostate cancer, Hodgkin's lymphoma, and other cancers, many of which are currently incurable with standard multimodality therapy. High incidence of p53 mutations and bcl-2 protein over-expression in breast cancer increase resistance to chemotherapy and radiotherapy. Systemic, tumor-targeted radioimmunotherapy (RIT) has the potential to target tissue specifically and to deliver cancer-specific cytotoxic antibodies to widespread metastatic foci. However, studies in a human breast cancer xenograft model demonstrate that RIT, as a single agent, typically does not cure the tumors. Tumor penetration of radiolabeled antibodies may be non-uniform and may not be sufficient in all regions of the tumor to provide cure. The combination of RIT with other therapeutic modalities is currently being utilized, but the additional chemotherapy or external radiotherapy increases the risk of bone marrow toxicity, the major dose-limiting factor in RIT.

Antiangiogenic agents have been proposed as a treatment for tumors. These agents target genetically normal endothelial cells, which proliferate at a much higher rate during tumor angiogenesis compared to very low endothelial turnover rates in normal tissues. Antiangiogenic agents have been shown to increase therapeutic efficacy in conjunction with other chemotherapeutic agents and when used in combination with external radiotherapy. The $\alpha_v\beta_3$ integrin receptor, which binds several ligands via an RGD amino acid sequence, is expressed in normal vasculature, but is highly expressed on growing tumor vasculature, making it a potential target for antiangiogenic agents. High expression and activation of the $\alpha_v\beta_3$ integrin has also been correlated with the more metastatic and invasive breast tumors. Inhibition of $\alpha_v\beta_3$ activity by monoclonal antibody (MAb) and cyclic RGD pentapeptides has been shown to induce endothelial apoptosis, inhibit angiogenesis, and increase endothelial monolayer permeability. Inhibition of $\alpha_v\beta_3$ activity has been associated with decreased tumor growth in breast cancer xenografts and melanoma xenografts. Synergy of cyclic RGD pentapeptide with antibody IL-2 fusion protein has resulted in increased efficacy of therapy in murine models of melanoma, colon carcinoma and neuroblastoma. Selective tumor uptake has been demonstrated with radiolabeled cyclic RGD pentapeptides.

SUMMARY OF THE INVENTION

The present invention provides a method of treating a patient having a tumor, such as a prostate tumor, a breast tumor, a lymphoma, and the like. The method is a combined-modality radioimmunotherapy (CMRIT) treatment regime involving administering to the patient an antiangiogenic cyclo-(arginine-glycine-aspartic acid)-containing pentapeptide (cRGD pentapeptide) and a radioimmunotherapeutic agent (RIT). The method comprises a sequential treatment regime including a first step of administering to a patient at least one dose of a cRGD pentapeptide. Following this initial cRGD pentapeptide treatment, the patient is administered an anti-tumor effective amount of a RIT. After the RIT treatment, the patient is administered at least one additional dose of cRGD pentapeptide.

The amount and timing of each cRGD pentapeptide dose is preferably chosen to be at or near the maximum tolerable dose to the patient, i.e., the maximum level at which the toxicity of the cRGD pentapeptide to the patient is therapeutically acceptable.

The CMRIT method of the present invention affords a significantly greater anti-tumor efficacy relative to treatment with the RIT alone or the cRGD pentapeptide alone, at the same dosage levels. The CMRIT method also provides greater apoptosis of the tumor cells and tumor endothelial cells relative to treatment with the RIT alone or the cRGD pentapeptide alone, at the same dosage levels.

In one aspect, the present invention also provides a kit comprising a first container including at least one unit dose of a RIT and one or more additional containers including a total of at least two unit doses of cRGD pentapeptide. The containers each include a label describing the contents of the container, optionally, sequences of administration, and any other pertinent information required by government regulations relating to pharmaceuticals and radioactive substances. The kit can also include printed instructions for use of the container contents for treatment of tumors according to the methods described herein.

DETAILED DESCRIPTION OF PREFERRED EMBODIMENTS

The present invention is susceptible of embodiment in many different forms. Specific embodiments are shown in the drawings and described in detail in the specification and claims. The present disclosure is an exemplification of the principles of the invention and is not limited to the specific embodiments that are illustrated herein.

A combined-modality radioimmunotherapy (CMRIT) method for treating tumors in a patient comprises the sequential steps of:

(a) administering to the patient at least one dose of an antiangiogenic cyclo-(arginine-glycine-aspartic acid)-containing pentapeptide (cRGD pentapeptide);

(b) administering to the patient an anti-tumor effective amount of a radioimmunotherapeutic agent (RIT); and (c) administering to the patient at least one additional dose of cRGD pentapeptide.

The amount and timing of each cRGD pentapeptide dose is preferably chosen to be at or near the maximum tolerable dose to the patient, i.e., the maximum level at which the toxicity of the cRGD pentapeptide to the patient is therapeutically acceptable. The maximum tolerable dose can readily be determined by methods well known in the pharmaceutical art. For example, the toxicity of the cRGD pentapeptide can be obtained from a clinical study. The amount of each dosage is preferably in the range of about 0.05 mg to about 500 mg, more preferably about 0.1 to about 100 mg, most preferably about 0.2 to about 20 mg. The daily aggregate dosage is preferably in the range of about 0.001 to about 2 mg/kg of body weight, more preferably about 0.002 to about 1 mg/kg, most preferably about 0.002 to about 0.2 mg/kg. The specific dose for each intended patient depends, however, on many factors, for example on the activity of the specific cRGD pentapeptide compound employed, the age, body weight, general state of health, sex, the diet, the time and rout of administration, and the rate of excretion, pharmaceutical combination, and severity of the particular disorder to which the therapy applies. Parenteral administration is preferred, most preferably intraperitoneal (i.p.) administration, however, oral, suppository, or topical administration are also contemplated. Additional cRGD pentapeptide doses can be continued for up to several months after administration of the RIT, if desired.

The cRGD pentapeptide can be formulated with pharmaceutically acceptable exipients and carriers, such as buffers, and the like, as is well known in the art. Suitable exipient substances are organic or inorganic substances which are suitable for enteral (e.g. oral or rectal), parenteral (e.g. intravenous injection) or local (e.g. topical, dermal, ophthalmic or nasal) administration or for administration in the form of an inhalation spray and which do not react with the novel compounds, examples being water or aqueous isotonic saline solution, lower alcohols, vegetable oils, benzyl alcohols, polyethylene glycols, glycerol triacetate and other fatty acid glycerides, gelatine, soya lecithin, carbohydrates such as lactose or starch, magnesium stearate, talc, cellulose and petroleum jelly.

For oral application, plain tablets, coated tablets, capsules, syrups, juices or drops are particularly useful; coated tablets and capsules having enteric coatings or capsule shells are especially of interest. Suppositories are used for rectal administration, solutions for parenteral administration, preferably oily or aqueous solutions, and also suspensions, emulsions or implants.

Examples of forms suitable for topical application are solutions, which can be used in the form of eye drops, and also, for example, suspensions, emulsions, creams, ointments or compresses. For administration in the form of an inhalation spray it is possible to use sprays which contain the active principle either dissolved or suspended in a propellant gas or propellant gas mixture (e.g. carbon dioxide or fluorochlorohydrocarbon substitutes). In this case the active principle is expediently used in micronized form, with the presence of one or more additional, physiologically compatible solvents, such as ethanol, being possible. Inhalation solutions can be administered with the aid of customary inhalers. The cRGD pentapeptide can also be lyophilized and the resulting lyophilisates used, for example, for producing injectable preparations. The injections can be given as a bolus or in the form of a continuous infusion (for example intravenous, intramuscular, subcutaneous or intrathecal). The preparations stated can be sterilized and/or can comprise auxiliaries such as preservatives, stabilizers and/or wetting agents, emulsifiers, salts for influencing the osmotic pressure, buffer substances, colorants and/or flavorings. If desired the cRGD pentapeptide can also contain one or more other active ingredients, including for example one or more vitamins, and the like.

The cRGD pentapeptide can be utilized per se or as one or more of its physiologically acceptable salts. The cRGD pentapeptide can be converted into an inner salt or into an associated acid addition salt using an acid. Suitable acids for this reaction are, in particular, those which yield physiologically acceptable salts. Thus inorganic acids can be used, examples being sulfuric acid, nitric acid, hydrohalic acids such as hydrochloric acid or hydrobromic acid, phosphoric acid such as orthophosphoric acid, sulfamic acid, and also organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, laurylsulfuric acid.

Alternatively, an acid form of the cRGD pentapeptide can be converted into one of its physiologically acceptable metal or ammonium salts by reaction with a base. Particularly suitable salts in this context are the sodium, potassium, magnesium, calcium and ammonium salts, and also substituted ammonium salts, for example the dimethyl-, diethyl- or diisopropylammonium salts, monoethanol-, diethanol- or triethanolammonium salts, cyclohexylammonium salts, dicyclohexylammonium salts, dibenzylethylenediammonium salts, and also, for example, salts with N-methyl-D-glucamine or with arginine or lysine Preferably the cRGD pentapeptide is cyclo-(Arg-Gly-Asp-D-Phe-Val) (EMD 66203), cyclo-(Arg-Gly-Asp-D-Phe-[N-Me]-Val) (EMD 121974, Cilengitide, available from Merck KGaA, Darmstadt, Germany), or cyclo-(Arg-Gly-Asp-D-Phe-1-aminocyclohexane carboxylic acid) (EMD 270179), the preparation of which are described in U.S. Pat.

Nos. 5,866,540 and 6,001,961 to Jonczyk et al., the relevant disclosures of which are incorporated herein by reference. Most preferably the cRGD pentapeptide is cyclo-(Arg-Gly-Asp-D-Phe-[N-Me]-Val).

Preferably, the first dosage of cRGD pentapeptide is administered to the patient no later than about 1 hour before administration of the RIT. Preferably, at least one additional dose of cRGD pentapeptide is administered within about two days after administration of the RIT. In a preferred embodiment, at least about two additional doses of cRGD pentapeptide are administered to the patient after the RIT dose, more preferably at least about 3 additional doses of cRGD pentapeptide, most preferably at least about 4 additional doses. In a particularly preferred embodiment, at least about five additional doses of cRGD pentapeptide are sequentially administered after the RIT dose. Preferably each additional dose of cRGD pentapeptide is administered at intervals of no more than about two days between doses. Administration of additional doses of RIT can be continued for periods of several months at a rate of about 2 doses per week, if desired.

The RIT dosage is preferably based upon the radioactivity level of the particular RIT agent. The amount of RIT utilized preferably provides a radioactive dosage in the range of about 20 mCi to about 200 mCi per dose when utilizing $^{90}Y$ as the source of radiation. The specific dose for each intended patient depends, however, on many factors, for example, on the radioactivity of the specific RIT compound employed, the particular radionuclide employed, the age, body weight, general state of health, sex, the diet, the time and route of administration, and the rate of excretion, pharmaceutical combination, and size and severity of the particular tumor to which the therapy ids being applied. For example, in treating metastatic prostate cancer or breast cancer, an anti-MUC-1 (M170) monoclonal antibody conjugated with chelated $^{90}Y$ is typically administered at a specific activity of about 5 mCi/mg of antibody to deliver a total dosage in the range of about 20 mCi to about 200 mCi depending on the size of the tumor and other factors described above. Parenteral administration of the RIT is preferred, more preferably intravenous (i.v.) administration.

Radioimmunotherapeutic agents for the treatment of tumors are well known in the art. Suitable RIT agents include any targeted radionuclide therapy with any therapeutically useful radionuclide attached, and which are attachable to or capturable by a tumor or tumor vasculature. Such useful RIT agents include a tumor-targeting or tumor vasculature-targeting ligand or molecule. The radionuclide can be attached directly to the targeting molecule or ligand, or by a chelating agent attached to or associated with the ligand. Alternatively, the ligand can include a chelating or radionuclide capturing group, and can be administered to the patient cold, to bind to a tumor or tumor vasculature in the patient. Upon subsequent administration of a radionuclide, the bound ligand can capture the radionuclide at the tumor site (pre-targeted radionuclide therapy). Targeting molecules or ligands include antibodies, antibody fragments, recombinant combinations of antibody fragments, peptides, or any other ligand that has a selective affinity for tumors or tumor vasculature.

Preferably the RIT is a radionuclide-labeled chelating agent-ligand complex in which chelating agent is chemically bonded to a tumor-targeting molecule. Preferred tumor-targeting molecules include antibodies, such as monoclonal antibodies, or antibody fragments. More preferably, the tumor-targeting molecule is an anti-tumor antibody. Any anti-tumor antibody can be utilized. Preferably, the anti-tumor antibody targets tumor vasculature. Alternatively, the antibody can target tumor antigens such as $p185^{HER2}$, milk mucin core protein, TAG-72, Lewis a, carcinoembryonic antigen (CEA), the high Mr melanoma antigens recognized by the 9.2.27 antibody, or the ovarian-associated antigens recognized by OV-TL3 or MOV18. Preferred anti-tumor antibodies are anti-MUC-1 monoclonal antibodies such as M170 mAb, available from Biomira Inc., Edmonton, Canada, a chimeric L6 anti-tumor monoclonal antibody (ChL6 MAb), and the like.

Any radionuclide suitable for use in cancer radiotherapeutic methods can be utilized in the CMRIT method of the present invention. Suitable radionuclides include, without limitation, $^{131}I$, $^{177}Lu$, $^{67}Cu$, $^{64}Cu$, $^{196}Re$, and $^{90}Y$. Preferably, the radionuclide is $^{90}Y$.

Suitable RIT agents and their preparation are described in U.S. Pat. No. 5,958,374 to Meares et al., the relevant disclosure of which is incorporated herein by reference.

Preferably the chelating agent is a polyazamacrocyclic group or a polyoxamacrocyclic group. More preferably the chelating group is derived from:

1,4,7,10-tetraazacyclododecane-N,N',N'',N'''-tetraacetic acid;

1,4,7,10-tetraazacyclotridecane-N,N',N'',N'''-tetraacetic acid;

1,4,8,11-tetraazacyclotetradecane-N,N',N'',N'''-tetraacetic acid; or 1,5,9,13-tetraazacyclohexadecane-N,N',N'',N'''-tetraacetic acid.

More preferably the radionuclide-labeled chelating agent-ligand complex is chemically bonded to ChL6 mAb or to M170 mAb. Most preferably the RIT is $^{90}Y$-1,4,7,10-tetraazacyclododecane-N,N',N'',N'''-tetraacetic acid-peptide-ChL6 (hereinafter, $^{90}Y$-DOTA-peptide-ChL6), or the anti-MUC-1 mAb analog thereof.

The radionuclide is preferably $^{90}Y$. $^{111}In$ can be included in the RIT to image the tumor. Preferably the radionuclide-labeled chelating agent-ligand complex is chemically bonded to ChL6 MAb or M170 mAb.

In a preferred embodiment the chelating agent is N-substituted 1,4,7,10-tetraazacyclododecane-N,N',N'',N'''-tetraacetic acid; wherein the N-substituent is —CH$_2$C(=O)-(Gly)$_3$-L-(p-isothiocyanato)-Phe-amide (hereinafter DOTA-peptide) and the radionuclide is $^{90}Y$.

The RIT can be formulated with a variety of pharmaceutically acceptable exipients suitable for a liquid injectable formulation as described above in relation to the formulation of the cRGD pentapeptides.

The CMRIT method of the present invention can be utilized to treat a variety of cancers. For example, the CMRIT method of the present invention can be utilized to treat cancers that manifest solid tumors such as breast cancer, colon cancer, lung cancer, thyroid cancer, ovarian cancer and the like. The CMRIT method can also be utilized to treat non-solid tumor cancers such as non-Hodgkin's lymphoma, and the like. The CMRIT method of the present invention is preferably utilized as a treatment for breast cancer.

The CMRIT method of the present invention affords a significantly greater anti-tumor efficacy relative to the aggregate total anti-tumor efficacy of treatment with the RIT alone and the cRGD pentapeptide alone, at the same dosage levels (i.e. a synergistic effect is observed). The CMRIT method also provides greater apoptosis of the tumor cells and tumor endothelial cells relative to treatment with the RIT alone or the cRGD pentapeptide alone, at the same dosage levels.

The present invention, in another aspect, provides a kit comprising a first container including at least one unit dose of a RIT and one or more additional containers including a total of at least two unit doses of cRGD pentapeptide. The containers each include a label describing the contents of the container, optionally the sequence of administration, and any other pertinent information required by government regulations relating to pharmaceuticals and radioactive substances. The kit can also include printed instructions for administration of the container contents for treatment of tumors according to the methods described herein.

The containers can be vials, ampules, bottles, and the like. Each container preferably includes a single unit dose, however, multi-dose containers can also be utilized. The instructional materials also preferably include safety and efficacy information.

The following non-limiting examples are provided to further illustrate the invention.

Reagents. Carrier-free yttrium-90 ($^{90}$Y) (Pacific Northwest National Laboratory, Richland, Wash. or New England Nuclear, Boston, Mass.) was purchased as the chloride salt in 0.05 M HCl. Chimeric L6 (ChL6), a human-mouse antibody chimera (Bristol-Myers Squibb Pharmaceutical Research Institute, Seattle, Wash.), reacts with an integral membrane glycoprotein highly expressed on human breast, colon, ovary, and lung carcinomas. Cyclo-(Arg-Gly-Asp-D-Phe-[N-Me]-Val) (EMD 121974) is an antagonist selective for $\alpha_v\beta_3$ and $\alpha_v\beta_5$ integrins, with $IC_{50}$ values in the low nanomolar range for isolated $\alpha_v\beta_3$ integrins and in the low micromolar range for $\alpha_v\beta_3$-expressing M21 melanoma cells. Peptide synthesis and characterization were performed as previously described by Dechantsreiter et al. *J. Med. Chem.* 42:3033–40 (1999), the relevant disclosure of which is incorporated herein by reference.

Cell Lines. HBT 3477, a human breast adenocarcinoma cell line, was obtained from Bristol-Myers Squibb Pharmaceutical Research Institute (Seattle, Wash.). Greater than 70% of HBT 3477 cells stain intensely with L6. In HBT 3477 cells, bcl-2 is expressed and p53 is mutant, with a nonsense mutation in exon 10, resulting in a deletion in the region of the p53 protein that functions in tetramerization and in detection of double-stranded DNA breaks. HBT 3477 cells express functional $\alpha_v\beta_5$ integrin, but not $\alpha_v\beta_3$ integrin, as attachment to vitronectin is blocked by $\alpha_v\beta_5$-specific P1F6 antibody, but is not blocked by $\alpha_v\beta_3$-specific LM609 antibody. Cyclo-(Arg-Gly-Asp-D-Phe-[N-Me]-Val) blocks attachment of HBT 3477 cells to vitronectin with an $IC_{50}$ of about 5 μM.

$^{90}$Y-DOTA-peptide-ChL6. ChL6 was conjugated to 1,4,7,10-tetraazacyclododecane-N,N',N'',N''' "-tetraacetic acid (DOTA) and radiolabeled with $^{90}$Y as described by DeNardo, et al. *J. Nucl. Med.*, 36:829–836, with greater than or equal to 80 percent efficiency to prepare $^{90}$Y-DOTA-peptide-ChL6. $^{90}$Y-DOTA-peptide-ChL6 was examined for structural and functional integrity by molecular sieving high performance liquid chromatography (HPLC), cellulose acetate electrophoresis (CAE), and HBT 3477 cell binding radioimmunoreactive assay (RIA). HPLC and CAE indicated that greater than 90% of $^{90}$Y-DOTA-peptide-ChL6 was in monomeric form with less than 4% high molecular weight species as determined by CAE. Immunoreactive binding to live cells indicated greater than 92% reactivity; administration as a single dose of 200, 230 or 260 ‖Ci $^{90}$Y-DOTA-peptide-ChL6.

Mice. Female athymic Balb/c nu/nu mice (7–10 week old; Harlan Sprague Dawley, Inc., Frederick, Md.) were maintained according to University of California animal care guidelines. HBT 3477 cells ($3.0\times10^6$), harvested in log phase, were injected subcutaneously into one side of the abdomen for therapy studies (except where noted) and into both sides for immunopathology studies. Injection of RIT was by tail vein and cyclo-(Arg-Gly-Asp-D-Phe-[N-Me]-Val) was delivered by intraperitoneal (i.p.) injection. "Day 0" was designated as the time of RIT injection or, for first cRGD pentapeptide injection, for cRGD pentapeptide only group. Mice were sacrificed by cervical dislocation for immunopathology studies at the times indicated, when tumor burden exceeded allowed limits, or at 84 days for therapy studies.

Control (No RIT) Treatment groups. Groups consisted of mice receiving no treatment (24 mice, 14 mice bearing 2 tumors each and 10 mice bearing 1 tumor); unlabeled ChL6 antibody (315 μg) (8 mice bearing 2 tumors each); and cyclo-(Arg-Gly-Asp-D-Phe-[N-Me]-Val), given in 6 doses of 250 μg on days 0, 2, 4, 6, 8, and 10 (18 mice, each with 1 tumor).

High Dose RIT Treatment groups. Groups consisted of mice receiving RIT as a single agent (260 μCi $^{90}$Y-DOTA-peptide-ChL6, (39 mice, 15 bearing 2 tumors each and 24 bearing 1 tumor)); and RIT (260 μCi $^{90}$Y-DOTA-peptide-ChL6) combined with cyclo-(Arg-Gly-Asp-D-Phe-[N-Me]-Val) in 6 doses of 250 μg, starting on day 0, 1 hour prior to RIT, followed by 5 more doses on days 2, 4, 6, 8, and 10 (42 mice, all with 1 tumor each).

Low Dose RIT Treatment groups. Groups consisted of mice receiving RIT as a single agent (200–230 μCi $^{90}$Y-DOTA-peptide-ChL6, (28 mice, including 9 bearing 2 tumors each from a previous study which received 230 μCi $^{90}$Y-DOTA-peptide-ChL6 and 19 mice bearing 1 tumor each treated with 200 μCi $^{90}$Y-DOTA-peptide-ChL6)); and a group receiving RIT (200 μCi $^{90}$Y-DOTA-peptide-ChL6) combined with six doses (250 μg each) of cyclo-(Arg-Gly-Asp-D-Phe-[N-Me]-Val). These doses were given on day 0, 1 hour prior to RIT, followed by 5 more doses on days 2, 4, 6, 8, and 10 (30 mice, all with 1 tumor each).

Tumoricidal effect. Tumors were measured with calipers in 3 orthogonal diameters 3 times per week. Tumor volume was calculated using the formula for hemiellipsoids (DeNardo et al. *Clin. Cancer Res.*, 3:71–79 (1997)). Initial tumor volume was defined as the volume on the day before treatment. Tumors that completely regressed were considered to have a volume of zero. Tumor responses were categorized as follows: cure (C), tumor disappeared and did not regrow by the end of the study (84 days); complete regression (CR), tumor disappeared for at least 7 days, but later regrew; partial regression (PR), tumor volume decreased by 50% or more for at least 7 days but then regrew; non-responsive (NR), tumor volume decreased less than 50%. For mice bearing two tumors with differing responses, tumor response was described according to both tumor responses. Mice dying prior to 30 days from toxicity were excluded from tumor response results.

Toxicity. Weights and blood counts were measured 2–3 times per week for 12 weeks post-injection or until death. Blood samples were collected from tail veins using 2 μL microcapillary pipets. Samples from mice within a dose group were pooled, and diluted 1:200 in phosphate-buffered saline (PBS, 0.9% saline/10 mM sodium phosphate, pH 7.6) for red blood cell (RBC) counts; 1:100 in 1% (w/v) ammonium oxalate for platelet counts; or 1:20 in 3% (w/v) acetic acid for white blood cell (WBC) counts.

Cellular immunopathology groups. Unless otherwise noted, groups consisted of 2 mice, each bearing 2 tumors, for a total of 4 tumors analyzed at each time point. The groups consisted of mice receiving no treatment (4 mice, 7 tumors); 250 μg cyclo-(Arg-Gly-Asp-D-Phe-[N-Me]-Val), given as single dose followed by sacrifice at 2 hours, 6 hours, and 1–5 days following peptide injection; RIT only (260 μCi $^{90}$Y-DOTA-peptide-ChL6) followed by sacrifice at 2 hours, 6 hours, and 1–6 days (3 mice, 5 tumors at 5 days); and RIT (260 μCi $^{90}$Y-DOTA-peptide-ChL6) combined with cyclo-(Arg-Gly-Asp-D-Phe-[N-Me]-Val) (250 μg) given 1 hour prior to RIT (CMRIT method), and repeated every other day through 10 days, followed by sacrifice at 2 hours, 6 hours, and 1–6 days after RIT. The tumors were removed, cut in half, frozen in optimal cutting temperature (O.C.T). medium, and stored at about −70° C. until sectioning (10-μm sections). All time points were evaluated for apoptosis by terminal deoxynucleotidyl transferase-mediated dUTP nick end labeling (TUNEL, Cavrieli, et al. *J. Cell Bio.*, 119: 493–501 (1992)) analysis, and selected time points (untreated, 1,5 and 6 days) were assessed for differences in proliferation rate (Ki67) and microvessel density (CD31).

TUNEL analysis of total and endothelial apoptosis. Tumors were cut into 10-μm sections onto Fisher superplus slides (Fisher, Pittsburgh, Pa.), air-dried for 1 hour and frozen at about −70° C. until TUNEL analysis with ApopTag Red kit (rhodamine used as label, Intergen, Purchase, N.Y.) following the manufacturer's instructions subsequent to fixation for about 10 minutes in 1% paraformadehyde. After TUNEL, the slides were rinsed, and incubated overnight at 4° C. with a rat anti-mouse MAb against CD31 at 1:100 dilution (Pharmingen, San Diego, Calif.) to identify endothelial cells. Slides were rinsed and incubated for 1 hour with an anti-rat antibody linked to FITC (1:50 dilution) (Pharmingen). Slides were rinsed, dipped briefly in 4,6-diamidino-2-phenylindole (DAPI, 0.2 μg/ml) for background nuclear stain, rinsed again and mounted, followed by storage in the dark at about 4° C. until quantitation.

Quantitation of total apoptosis and endothelial apoptosis. An Olympus microscope equipped with a Chroma Pinkle Filter Set (Chroma, Brattleboro, Vt.) with excitation filters for UV, FITC and rhodamine and dual/triple bandpass filters to allow simultaneous viewing of multiple wavelengths, was used to quantify 6 randomly chosen X600 fields (150,000 μm$^2$/field) in non-necrotic regions of each section. Fields were chosen to cover the entire viewing area using DAPI label, which typically included about 300–350 cells. Total apoptosis was determined by the average number of positive nuclei per field for each tumor while endothelial apoptosis was determined using the same fields with a dual bandpass filter to count cells labeled by both FITC (CD31) and rhodamine (TUNEL). Fields were chosen from apparently non-necrotic areas of tumor sections, as HBT 3477 xenografts typically grow quickly in nude mice, doubling their volumes in 6 days, resulting in central necrosis of untreated tumors. As TUNEL may label necrotic cells, though less intensely, this strategy was chosen over a completely random process.

Proliferation and microvessel density Analyses. 10-μm sections of tumors from untreated and mice treated with cRGD pentapeptide, RIT and CMRIT method and sacrificed at 1, 5 and 6 days after treatment were fixed for 10 minutes in ice-cold acetone, rinsed in PBS, and briefly incubated in methanol with 0.6% H$_2$O$_2$ (5 minutes). After rinsing in PBS, sections were blocked for 10 minutes with 10% goat serum and 1% bovine serum albumin in PBS. Mouse anti-Ki67 MAb (Pharmingen, clone B56) was applied in blocking solution (6.25 μg/ml) and the slides were incubated at room temperature for 2 hours, followed by rinsing in PBS. Goat anti-mouse rhodamine-labeled or goat anti-mouse Cy-3-labeled antibody was applied (Jackson ImmunoResearch Laboratories, Inc, West Grove, Pa., 1:100) and the slides were incubated for 1 hour at room temperature. After rinsing in PBS the sections were incubated for 1 hour at room temperature with rat anti-mouse CD31 antibody (Pharmingen, 1:100), followed by rinsing in PBS and a subsequent 1 hour incubation with goat anti-rat FITC-labeled antibody (Pharmingen, 1:50). After rinsing in PBS, the slides were counterstained with DAPI (0.4 μg/ml) and mounted in Biomeda gel mount (Fisher) under coverslips. Quantitation of Ki67 was performed using an Olympus microscope at X1000 magnification for assessment of proliferation. The mean total number of Ki67-positive cells/field in a tumor was determined by counts from 6 fields per tumor chosen randomly by DAPI stain. Microvessel density was determined by counting the number of CD31-stained vessels per random field at X400 magnification. Any endothelial cell or cell cluster positive for CD31, which was separate from an adjacent cluster, was counted as one microvessel. Six randomly chosen fields per tumor section were used to establish an average for each tumor. Average microvessel density for a treatment group was determined by averaging the values from 4 tumors/group.

$β_3$ and CD31 expression by HBT 3477 tumors in nude mice. Tumors were cut in half, frozen in O.C.T. medium (Tissue Tek, Miles, Inc., Elkhart, Ind.) and stored at about −70° C. until sectioning. Sections (10-μm) were air dried and frozen at about −70° C. until stained. Sections were then fixed in ice-cold acetone for 10 minutes, rinsed in PBS and blocked in 10% goat serum in PBS for 30 minutes. Hamster anti-mouse CD61 ($β_3$) MAb (Pharmingen) was applied at 10 μg/ml and the slides were incubated for 3 hours at room temperature. After rinsing in PBS, anti-hamster rhodamine-linked antibody (Jackson ImmunoResearch Laboratories, Inc.) was applied (1:50), followed by a 1 hour incubation at room temperature. After rinsing in PBS, rat anti-mouse CD31 antibody was applied (1:100, Pharmingen) and the slides were incubated for 1 hour at room temperature. Following PBS rinsing, anti-rat FITC-linked antibody (1:50, Pharmingen) was applied and the slides were incubated for 1 hour at room temperature and rinsed in PBS. The slides were dipped in DAPI (0.2 μg/ml) and mounted with Biomeda gel mount (Fisher) under coverslips. Coexpression of $β_3$ and CD31 was observed with an Olympus microscope equipped with a Chroma Pinkle Filter Set (Chroma, Brattleboro, Vt.) with excitation filters for UV, FITC and rhodamine and dual/triple bandpass filters to allow simultaneous viewing of multiple wavelengths.

Statistical Analysis. Statistical analysis of mortality data for RIT and CMRIT method treated mice was performed using a Fisher Exact test with StatExact software to determine if mortality was different. Statistical analysis of therapy data was done using a Cochran Mantel Haenszel test to evaluate effect of RIT dose on outcome for RIT and CMRIT method groups. Comparison of cure rates to all other responses for RIT vs. CMRIT method groups was done by Fisher Exact test, with the best tumor response used for 2-tumored animals for statistical purposes. Statistical differences between immunopathology groups at the different time points were assessed by analysis of variance (ANOVA) (Fisher PLSD) using STATview software as appropriate, with p<0.05 considered significant.

Tumoricidal effect. Most tumors in untreated mice, mice receiving cyclo-(Arg-Gly-Asp-D-Phe-[N-Me]-Val) alone, and mice receiving ChL6 unlabeled antibody grew without interruption. No apparent effect of cyclo-(Arg-Gly-Asp-D-Phe-[N-Me]-Val) (6×250 μg doses total given every other day) was observed on tumor growth, resulting in no cures in 18 mice tested. Two mice receiving unlabeled ChL6 antibody in addition to 2 untreated mice experienced spontaneous regression of their tumors, leading to a 8% (4/50) cure rate for non-RIT mice (Table 1, FIG. 1).

In Table 1, the numbers in parentheses represent totals obtained using the best response from mice which had two tumors (2-tumored mice). For example, if a 2-tumored mouse had one tumor cured and one tumor partially regresses, this would count as a partial regression (PR) in the table under a worst response analysis (entries without parenthesis), but would count as a cure (C) using the best response analysis (parenthetical numbers). Mice receiving RIT were treated with 260 µCi (high dose) or 200–230 µCi (low dose) $^{90}$Y-DOTA-peptide-ChL6 by itself or in combination with 6 doses of cyclo-(Arg-Gly-Asp-D-Phe-[N-Me]-Val) (CMRIT method). Tumor responses in mice dying from toxicity prior to 30 days after RIT were excluded from efficacy assessment. High dose RIT alone resulted in 4 cures in 26 mice (15%), while low dose RIT alone resulted in 5 cures in 20 mice (25%). The CMRIT method with low dose RIT resulted in 8 cures in 22 mice (36%, p=0.514) while CMRIT method with high dose RIT resulted in 10 cures in 19 mice (53%, p=0.011). Statistical analysis indicated that there was no difference in outcome of therapy based on RIT dose adjusted for RIT or CMRIT method. As outcome was not altered by dose (p>0.8), outcomes for RIT were compared to outcomes for the CMRIT method. The results show that the CMRIT method resulted in significantly more cures (44% cure rate) than RIT (20% cure rate) (p=0.020), consistent with increased efficacy of the CMRIT method over RIT alone.

Figure 1:
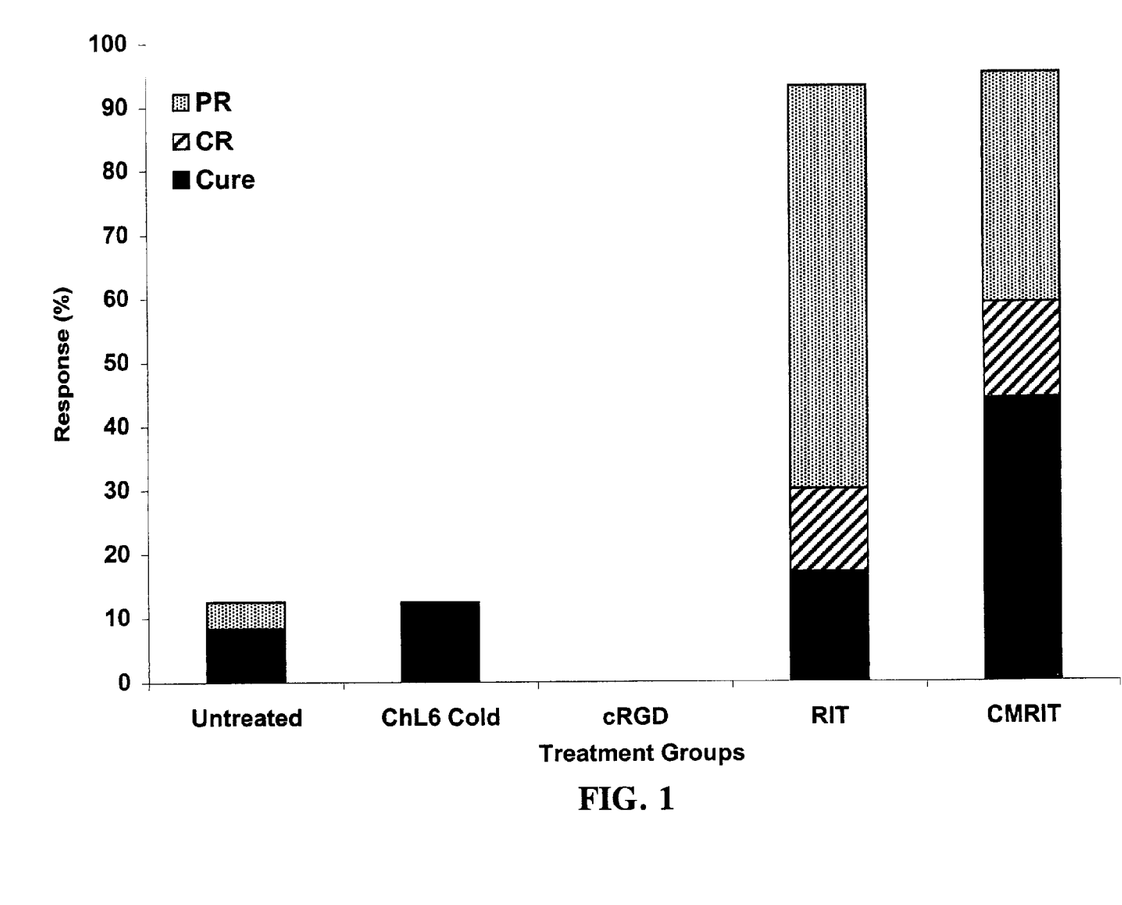
FIG. 1 is a bar graph that illustrates an increased tumor cure rate in mice treated with the CMRIT method of the present invention relative to treatments with RIT alone and CRGD pentapeptide alone, with PR denoting partial regression and CR denoting complete regression.

FIG. 1 depicts increased efficacy of treatment in mouse breast cancer xenografts is obtained with CMRIT method. Tumor responses to $^{90}$Y-DOTA-peptide-ChL6 and cyclo-(Arg-Gly-Asp-D-Phe-[N-Me]-Val) used as single agents and in combined therapy (CMRIT method) are shown. Results illustrate combined high dose and low dose results for RIT (200–260 µCi $^{90}$Y-DOTA-peptide-ChL6). Groups were untreated, mice treated with 315 µg unlabeled ChL6, mice treated with 6 doses of 250 µg of cyclo-(Arg-Gly-Asp-D-Phe-[N-Me]-Val), mice treated with RIT alone, and CMRIT method treated mice (6 doses of 250 µg cyclo-(Arg-Gly-Asp-D-Phe-[N-Me]-Val) and 1 dose RIT (200 and 260 µCi)). Responses were assessed at the end of 84 days. Significantly increased efficacy of treatment was observed in CMRIT method treated mice compared to RIT treated mice (using worst outcome, as shown, or best outcome for double-tumored mice, with p=0.02 for the latter).

Figure 2:
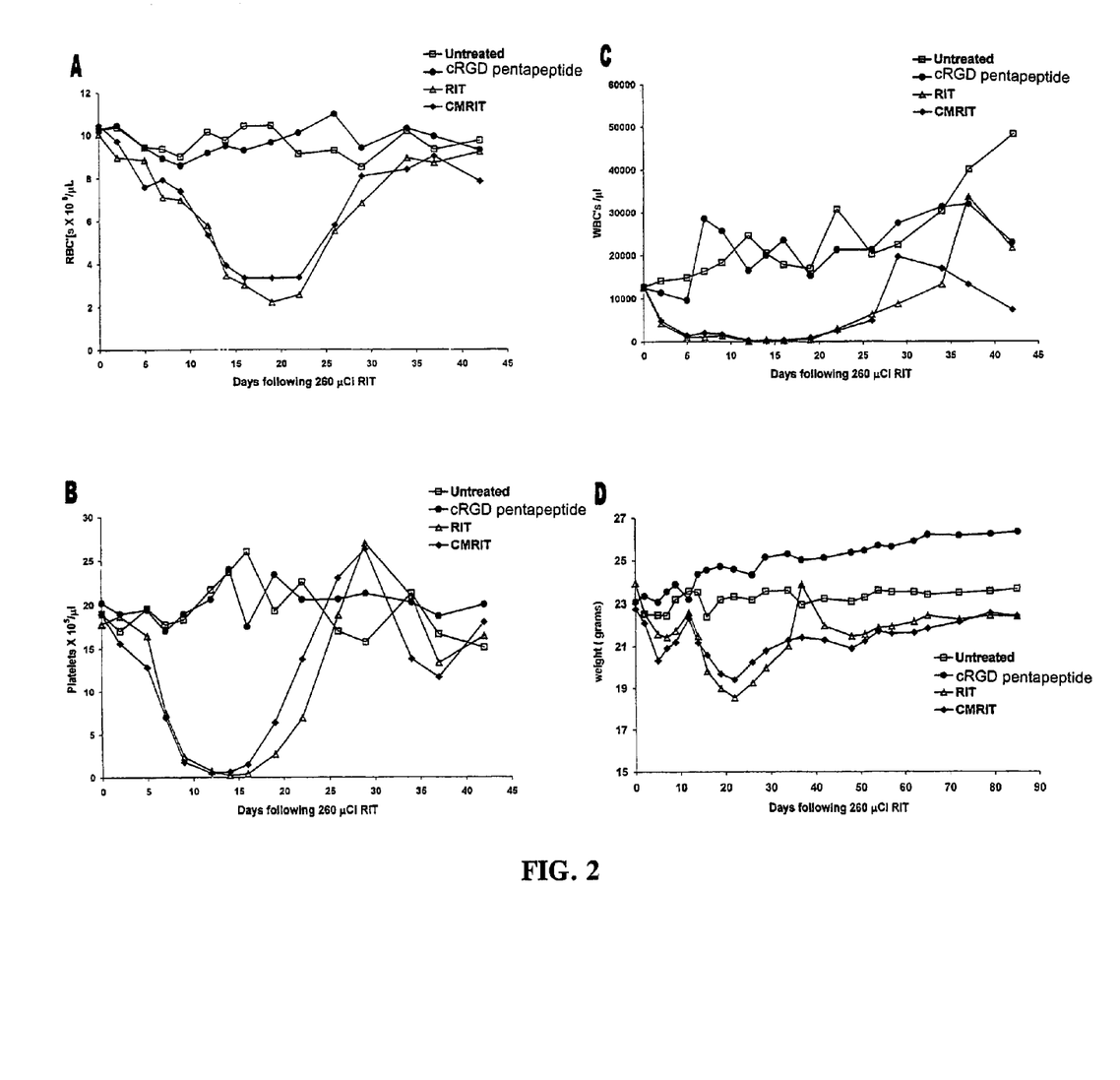
FIG. 2 provides graphical representations of toxicity data in mice treated with the CMRIT of the present invention in comparison with treatments of RIT alone and a cRGD pentapeptide alone.

Toxicity of Cyclo-(Arg-Gly-Asp-D-Phe-[N-Me]-Val). No increased mortality or toxicity was induced by cyclo-(Arg-Gly-Asp-D-Phe-[N-Me]-Val) (250 µg, 6 doses over 10 days) alone compared to untreated mice (no mice died from toxicity out of all the groups not receiving RIT (untreated, unlabeled ChL6, Cyclo-(Arg-Gly-Asp-D-Phe-[N-Me]-Val)). Cyclo-(Arg-Gly-Asp-D-Phe-[N-Me]-Val)-treated and untreated mice displayed similar weight changes and RBC, WBC and platelet levels. Mice treated with either high or low dose RIT and mice treated with the combination of RIT and cyclo-(Arg-Gly-Asp-D-Phe-[N-Me]-Val) demonstrated decreased weight, RBC, WBC and platelet counts compared to mice receiving no RIT, but the combination of RIT with cyclo-(Arg-Gly-Asp-D-Phe-[N-Me]-Val) did not depress these values beyond those observed with RIT alone (FIGS. 2A-D). At the high dose of RIT, mortality was higher than untreated mice in both RIT (13/39 mice (33%)) and the CMRIT method (23/42 mice (55%)) groups, but mortality was not statistically increased by the CMRIT method (Fisher Exact, p=0.0736). Likewise mortality was increased in low dose RIT and CMRIT method groups over untreated mice, but mortality of CMRIT method treated (8/30 (27%)) mice was not increased above RIT (8/28 mice (29%)) (Fisher's Exact, p=1.000). When low and high dose mortality results are combined, the CMRIT method does not result in increased mortality over RIT (Fisher's Exact, p=0.1652). These results indicate that a cRGD pentapeptide such as cyclo-(Arg-Gly-Asp-D-Phe-[N-Me]-Val), administered alone or in combination with RIT, does not significantly increase toxicity.

FIG. 2 shows that neither the cyclo-(Arg-Gly-Asp-D-Phe-[N-Me]-Val) therapy nor the CMRIT method increases toxicity. A: RBC, B: platelet, C: WBC, and D: mouse weights for groups of untreated mice (5), mice treated with cyclo-(Arg-Gly-Asp-D-Phe-[N-Me]-Val) (6 doses of 250 µg) alone (13), mice treated with RIT alone (260 µCi $^{90}$Y-DOTA-peptide-ChL6)(5), and mice treated with the CMRIT method (260 µCi $^{90}$Y-DOTA-peptide-ChL6 and 6 doses of 250 µg cyclo-(Arg-Gly-Asp-D-Phe-[N-Me]-Val)) (13) from a single trial. Results shown represent pooled blood samples for each group and average weights ±s.e for each group on days shown. The cRGD pentapeptide by itself or in combination with RIT did not increase toxicity.

Figure 3:
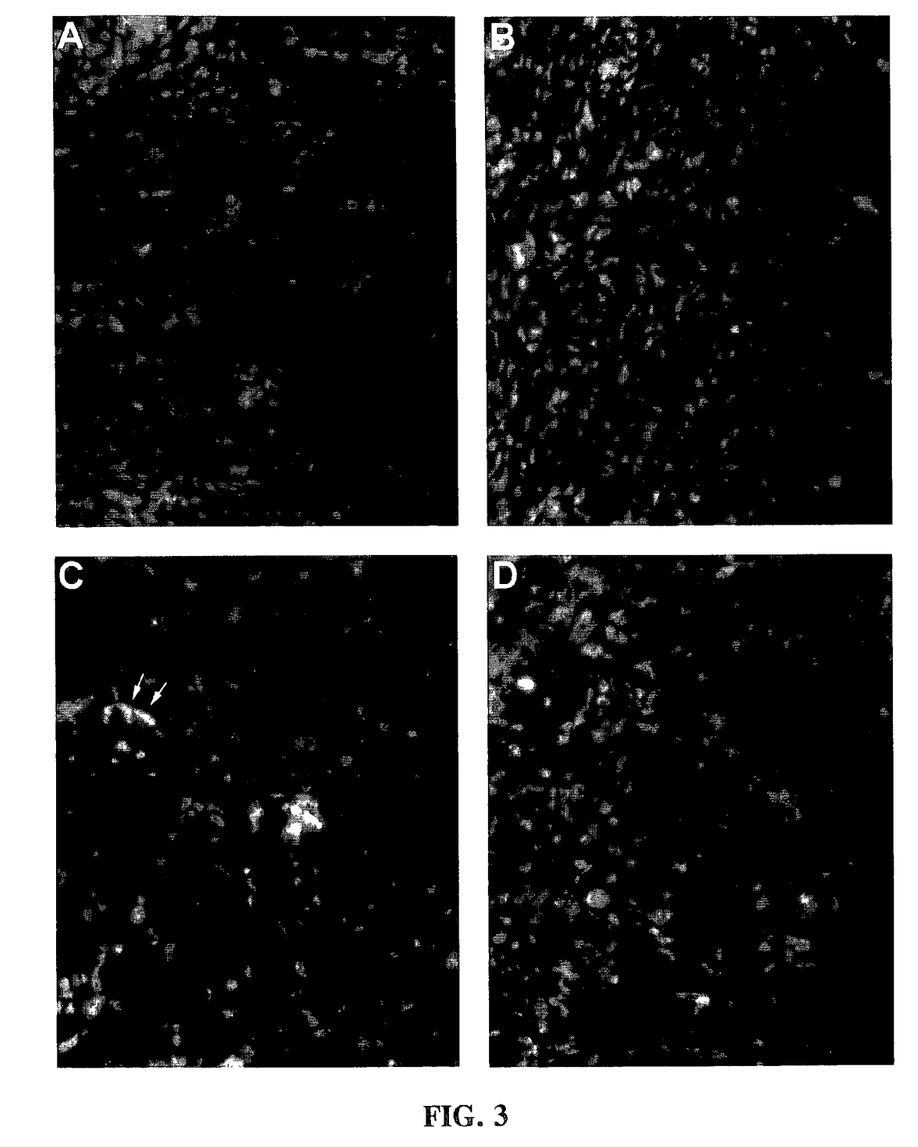
FIG. 3 depicts photomicrographic images of tumor cells, which demonstrate increased apoptosis in tumors from mice treated with the CMRIT method of the present invention.

Apoptosis in tumor and endothelial cells (total cell). Apoptosis was assessed by the TUNEL method in combination with CD31 staining to identify endothelial cells (FIG. 3). The number of TUNEL-positive tumor and endothelial cells (total cells) were averaged per tumor from 6 random fields (X600) of non-necrotic tissue, chosen such that cells

TABLE 1

| Treatment | cRGD pentapeptide | RIT (µCi) | # Mice | Cure | CR | PR | NR |
|---|---|---|---|---|---|---|---|
| No treatment | — | — | 24 | 2 | 0 (1) | 1 (3) | 21 (18) |
| ChL6, 315 µg | — | — | 8 | 1 (2) | 0 | 0 | 7 (6) |
| cRGD pentapeptide | 250 µg × 6 | — | 18 | 0 | 0 | 0 | 18 |
| RIT low dose | — | 200–230 | 20 | 4 (5) | 4 | 9 (11) | 3 (0) |
| RIT high dose | — | 260 | 26 | 4 | 2 (6) | 20 (16) | 0 |
| CMRIT low dose | 250 µg × 6 | 200 | 22 | 8 | 3 | 10 | 1 |
| CMRIT high dose | 250 µg × 6 | 260 | 19 | 10 | 3 | 5 | 1 |
| RIT (combined) | — | 200–260 | 46 | 8 (9) | 6 (10) | 29 (27) | 3 (0) |
| CMRIT (combined) | 250 µg × 6 | 200–260 | 41 | 18 | 6 | 15 | 2 |

In Table 1, cRGD pentapeptide is cyclo-(Arg-Gly-Asp-D-Phe-[N-Me]-Val); CR is complete regression, PR is partial regression, and NR is no regression; numbers inparenthesis based on best response from 2-tumored mice.

covered the entire area of the field, with an average of approximately 350 cells/field. Untreated tumors had an average of 9±1.0 positive cells/field (2.6%). A single dose of the cRGD pentapeptide (cyclo-(Arg-Gly-Asp-D-Phe-[N-Me]-Val)) significantly increased apoptosis 1 day after treatment (16.2±1.89, 4.6%), but this level of apoptosis subsequently decreased. Compared to untreated tumors, RIT alone resulted in significantly increased apoptosis (as noted on FIG. 4), with the greatest number of apoptotic cells seen at 6 days (21.4±2.9, 6.1%). Apoptosis following the CMRIT method was higher than all other treatment groups at all time points except 6 days (significantly increased apoptosis noted, FIG. 4). Apoptosis following the CMRIT method peaked at 5 days following RIT (30.7±2.0 cells/field, 8.8%), with a lower peak at 1 day after the CMRIT method (21.9±2.6, 6.3%). These two peaks of apoptosis are consistent with two "waves" of apoptosis occurring. However, the difference in total cell apoptosis occurring in CMRIT method treated tumors compared to RIT tumors is additive, and thus suggests other mechanisms may also affect efficacy.

FIG. 3 depicts photomicrographic images which demonstrate that CMRIT method results in increased apoptosis. Apoptosis (TUNEL with ApopTag Red) and CD31 (FITC) are illustrated in 10-µm sections of tumors from (A) untreated, (B) cRGD pentapeptide-treated (1 dose 250 µg cyclo-(Arg-Gly-Asp-D-Phe-[N-Me]-Val)), (C) RIT (260 µCi $^{90}$Y-DOTA-peptide-ChL6), and (D) CMRIT method (260 µCi $^{90}$Y-DOTA-peptide-ChL6 and 6 doses of 250 µg cyclo-(Arg-Gly-Asp-D-Phe-[N-Me]-Val)) mice assessed 5 days following start of treatment. Apoptosis (rhodamine) is observed in tumor cells and in endothelial cells (FITC) where rhodamine and FITC dyes are colocalized (orange cells marked by arrowheads). Background nuclear stain was obtained with DAPI. Sections were photographed at X600 with an Olympus microscope equipped with Pinkle filters. Increased apoptosis of tumor and endothelial cells was observed in CMRIT method treated mice compared to mice treated with RIT alone (ANOVA, p<0.05).

Figure 4:
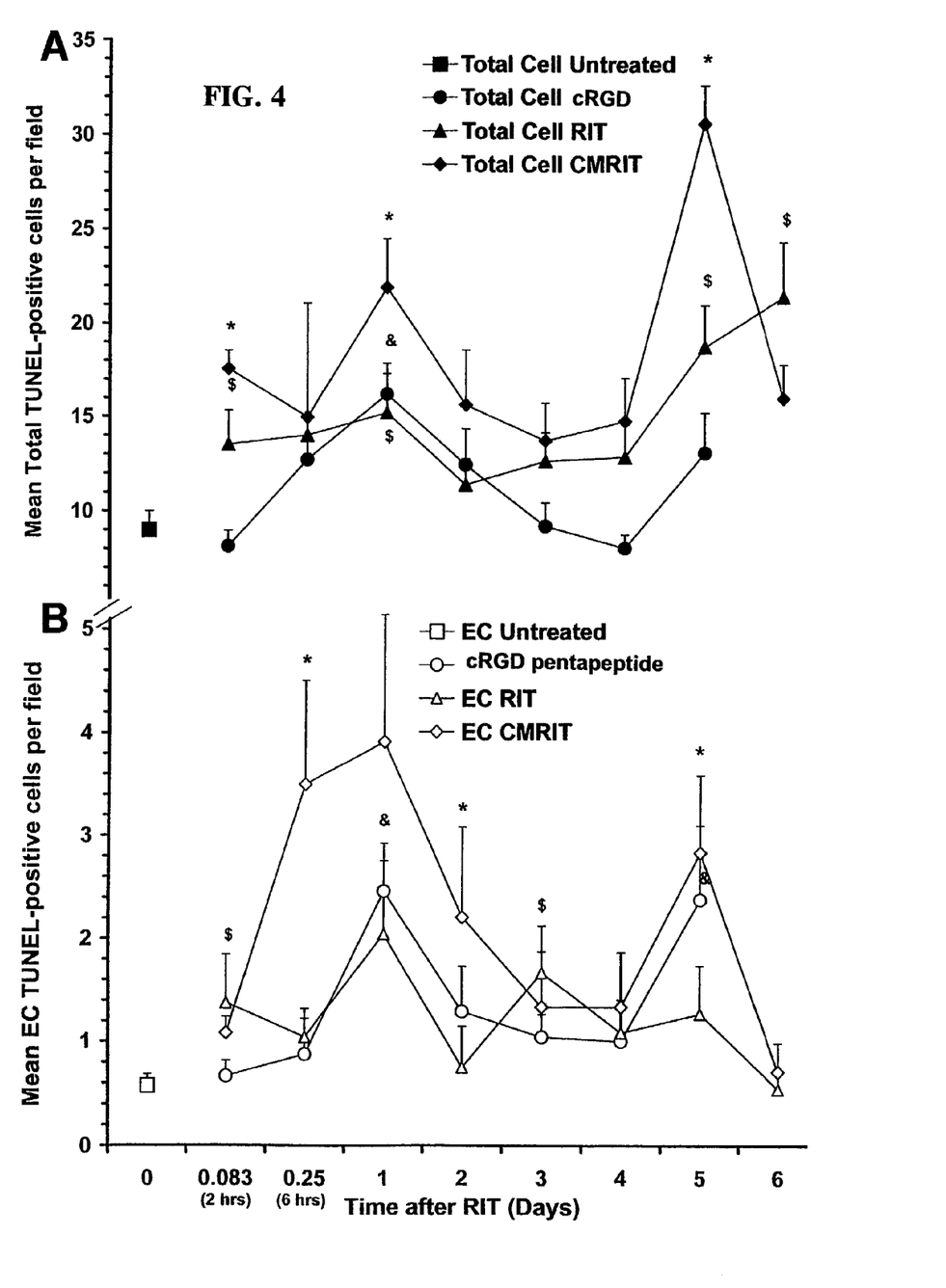
FIG. 4 provides graphical representations of data showing apoptosis in (A) total cells, and (B) endothelial cells (EC) in tumors from mice treated with the CMRIT method of the present invention, as determined by the TUNEL method.

Endothelial apoptosis. Since a cRGD pentapeptide has previously been reported to induce apoptosis in vascular endothelial cells endothelial apoptosis in cRGD pentapeptide-treated (single dose cyclo-(Arg-Gly-Asp-D-Phe-[N-Me]-Val)) tumors was compared to untreated tumors. Significantly increased apoptosis was observed 1 day (2.5±0.5) and 5 days (2.4±0.7) after cRGD pentapeptide treatment compared to untreated tumors (0.6±0.1). However, these differences in apoptosis between cRGD pentapeptide-treated and untreated tumors were not reflected by differences in growth or tumor volume even with multiple (6) doses of cyclo-(Arg-Gly-Asp-D-Phe-[N-Me]-Val). RIT alone also resulted in significantly increased endothelial apoptosis compared to untreated tumors at early time points (FIG. 4). CMRIT was associated with 2 peaks of endothelial cell apoptosis, 1 day and at 5 days after RIT, with the highest levels at 1 day (3.9±1.2 cells/field). (FIG. 4). The average level of endothelial apoptosis in CMRIT method treated tumors was higher than all other groups at all times, except 3 days and 6 days. However, increased endothelial apoptosis did not appear to precede total cell apoptosis in CMRIT method treated tumors, with peaks occurring in both at 1 and 5 days.

FIG. 4 provides graphical representations of data showing that cyclo-(Arg-Gly-Asp-D-Phe-[N-Me]-Val) results in increased apoptosis in tumor and endothelial cells at 1 and 5 days following cRGD pentapeptide treatment alone, or CMRIT method treatment. A. Apoptosis in total (closed symbols) and B. endothelial cells (EC) (open symbols) was assessed by TUNEL and CD31 immunohistochemical analysis in HBT 3477 tumors from untreated mice (■), mice treated with cRGD pentapeptide (1 dose 250 µg cyclo-(Arg-Gly-Asp-D-Phe-[N-Me]-Val))(●), mice treated with RIT (260 µCi $^{90}$Y-DOTA-peptide-ChL6)(▲), and mice treated with CMRIT method (260 µCi $^{90}$Y-DOTA-peptide-ChL6 and 6 doses of 250 µg cyclo-(Arg-Gly-Asp-D-Phe-[N-Me]-Val))(◆). Apoptosis was quantitated at X600 magnification from 6 random fields per tumor, with 4 tumors used for the determination of the treatment mean. Total cell apoptosis is indicated by solid markers and endothelial apoptosis by open markers. Error bars indicate standard error of the mean. CMRIT method values significantly greater (ANOVA, p<0.05) than RIT values are indicated by *;. cRGD pentapeptide values significantly greater than untreated (ANOVA, p<0.05) are indicated by &; RIT values significantly greater than untreated are indicated by $. Total cell apoptosis for CMRIT method treated tumors was significantly different from RIT tumors at 2 hours, 1 day and 5 days after RIT. Endothelial apoptosis was significantly increased in CMRIT method treated mice over RIT mice at 6 hours, 2 days and 5 days after RIT. The X-axis is not drawn to scale to illustrate changes at early time points. Break in the Y axis indicates change of scale between total cell apoptosis and endothelial cell apoptosis.

Total Cell Proliferation. The average number of Ki67-positive cells was determined for untreated tumors and for tumors at 1, 5 and 6 days (cRGD pentapeptide treated tumors were not determined on day 6). Ki67 antibody recognizes protein present in the nuclei of proliferating cells at all active stages of cell cycle, but does not recognize protein found in cells at $G_0$. The results indicate that RIT or cRGD pentapeptide alone significantly decreased proliferation rates of cells active in cell cycle at 5 days compared to untreated mice (Table 2). The CMRIT method similarly decreased proliferation compared to untreated mice, and resulted in significantly decreased proliferation at 6 days compared to RIT alone (FIG. 5).

Figure 5:
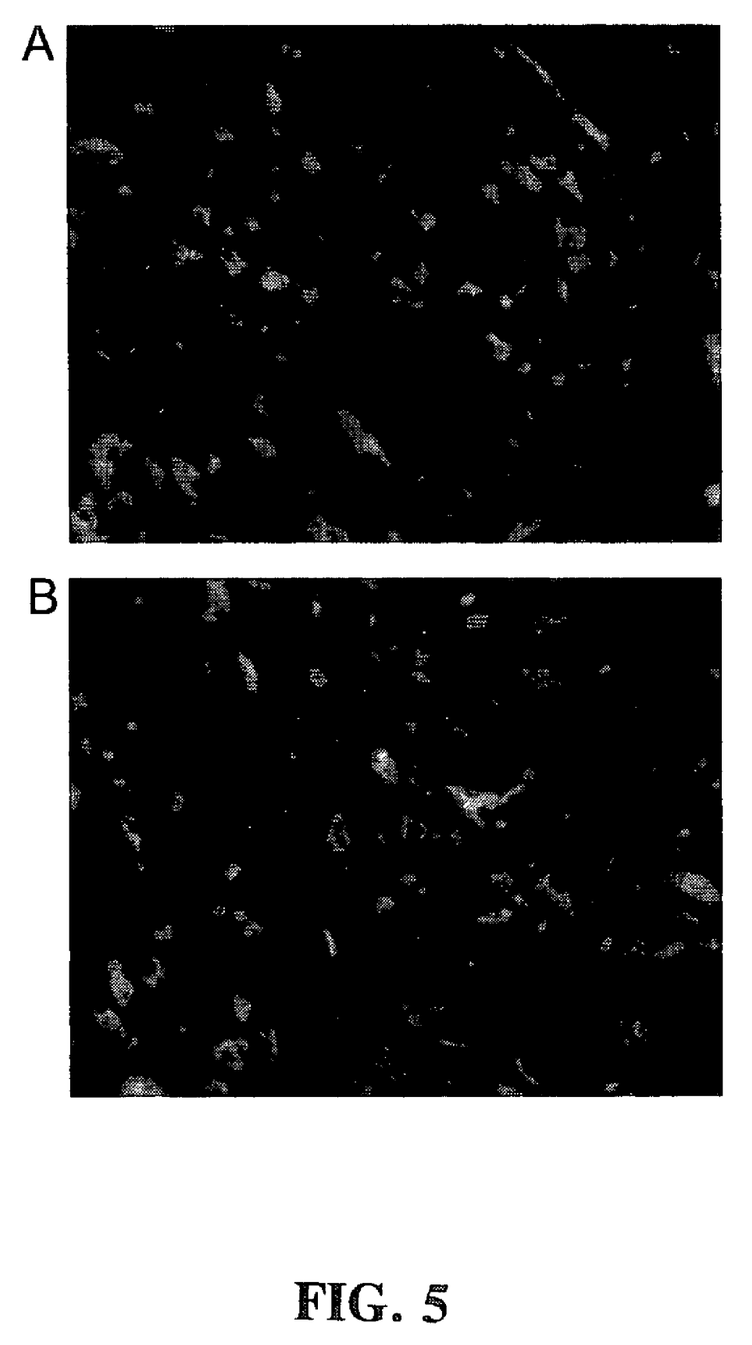
FIG. 5 depicts photomicrographic images of tumor cells, which demonstrate decreased cell proliferation in tumors from mice treated with the CMRIT method of the present invention relative to mice treated with RIT alone and a cRGD pentapeptide alone.

FIG. 5 depicts photomicrographic images of tumor cells demonstrating decreased proliferation of tumor cells following CMRIT method treatment vs. RIT treatment. Proliferating cells in (A) RIT and (B) CMRIT method treated tumors were identified on 10-µm frozen sections of tumors 6 days following RIT by Ki67 mouse MAb followed by anti-mouse rhodamine-linked antibody. Endothelial cell clusters used for microvessel density counts were identified by anti-CD31 rat MAb followed by anti-rat antibody linked to FITC. Nuclear stain was DAPI. Proliferation was quantitated at X1000 magnification from 6 random fields per tumor, with 4 tumors used for the determination of the treatment mean. Fewer Ki67-positive cells were observed in the CMRIT method treated tumors compared to RIT treated tumors 6 days following RIT, though the number of microvessels was not different at this time point. Sections were photographed at X600 with an Olympus microscope equipped with Pinkle filters.

Microvessel density. Microvessel density for each tumor was determined by averaging the total number of non-contiguous, CD31-stained regions in 6 randomly chosen fields from one section of each tumor from untreated mice, cRGD pentapeptide treated, RIT and CMRIT method treated mice at key time points after treatment (Table 2). Significantly decreased microvessel density compared to untreated mice was observed 6 days after RIT treatment in mice receiving either RIT alone or RIT combined with cRGD pentapeptide (cyclo-(Arg-Gly-Asp-D-Phe-[N-Me]-Val)). Increased endothelial apoptosis (above RIT) observed during Day 1 and at Day 5 did not appear to be associated with measurable differences in microvessel density, and did not precede total cell apoptosis. These data indicate that increased endothelial apoptosis associated with the CMRIT method may contribute to, but is not likely the only mechanism affecting therapeutic outcome. In addition, the data through Day 6 do not indicate that decreased microvessel counts explain the difference in therapeutic outcome between RIT and the CMRIT method.

TABLE 2

| Day | Untreated | cRGD a | RIT b | CMRIT c |
|---|---|---|---|---|
| Microvessel density d | | | | |
| 0 | 16 ± 3 | | | |
| 1 | | 12 ± 2 | 15 ± 1 | 15 ± 2 |
| 5 | | 20 ± 4 | 13 ± 1 | 12 ± 1 |
| 6 | | | 9 ± 1 e | 9 ± 2 e |
| Proliferating cells f | | | | |
| 0 | 17 ± 1 | | | |
| 1 | | 14 ± 2 f | 18 ± 1 | 19 ± 1 |
| 5 | | 13 ± 1 f | 13 ± 1 f | 13 ± 1 f |
| 6 | | | 7 ± 1 | 3 ± 1 g | a single ip dose of cyclo-(Arg-Gly-Asp-D-Phe-[N-Me]-Val), 250 μg.
b single iv dose of 315 μg 90Y-DOTA-peptide-ChL6 (260 μCi).
c single iv dose of 315 μg 90Y-DOTA-peptide-ChL6 (260 μCi) and 4 ip doses of 250 μg each of cyclo-(Arg-Gly-Asp-D-Phe-[N-Me]-Val) on alternate days starting 1 hour prior to RIT
d average number ± SE of CD31 positive regions in six fields for each tumor counted at 400X
e significantly different from untreated (ANOVA, $p < 0.05$)
f average no. of proliferating cells determined by taking average no. of Ki67-positive cells in six fields for each tumor counted at 1000X (about 112 ± 10 cells/field).
g CMRIT method significantly less than PIT (ANOVA, $p < 0.05$).

Figure 6:
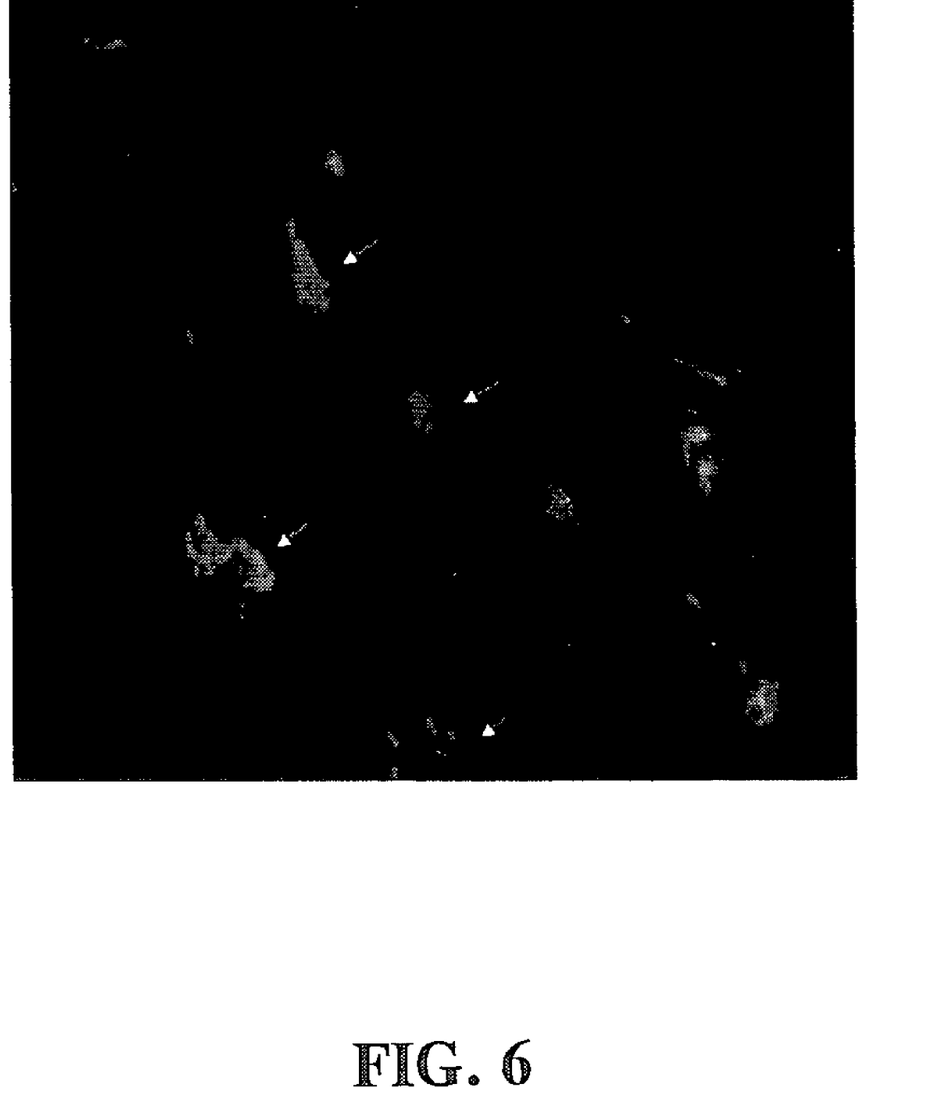
FIG. 6 depicts a photomicrographic image of HBT 3477 breast tumor cells, which illustrates $\beta_3$ and CD31 expression on the cells.

Expression of $\alpha_v\beta_3$ on HBT 3477 tumors. Immunohistochemistry with anti-$\beta_3$ antibody reactive with mouse integrin (CD61) demonstrated limited labeling of selected regions of HBT 3477 tumors in nude mice (FIG. 6). $\beta_3$-labeled regions included areas appearing as ring-like vascular structures, which were co-labeled by an antibody recognizing CD31, which is consistent with $\alpha_v\beta_3$ expression in the blood vessels supplying these tumors. Substantially less expression of $\beta_3$ was observed than CD31, which would be expected if only a small proportion of endothelial cells labeled by CD31 were neovascular.

FIG. 6 is a photomicrographic image of a tumor section showing that $\beta_3$ and CD31 are expressed on HBT 3477 breast cancer tumor cells. The tumor removed from an untreated mouse was analyzed for expression of integrin P and endothelial protein CD31 using immunohistochemical techniques. Hamster MAb to mouse $\beta_3$ was applied followed by anti-hamster rhodamine-linked antibody. Subsequently rat anti-mouse CD31 MAb was applied followed by anti-rat FITC-linked antibody. Colocalization (orange color, indicated by arrows) of rhodamine ($\beta_3$) and FITC (CD31) is consistent with $\alpha_v\beta_3$ integrin expression in the blood vessels supplying the tumor. Tumor section was photographed at X600 with an Olympus microscope equipped with Pinkle filters.

The results demonstrate that the CMRIT method of the present invention increased the efficacy of tumor treatment without increased toxicity relative to conventional RIT monotherapy. The CMRIT method utilizing a high dose of RIT resulted in 53% cures compared to 15% cures for RIT alone, and 0% cures for cyclo-(Arg-Gly-Asp-D-Phe-[N-Me]-Val) alone, while combined dose levels resulted in 44% cures compared to 20% cures for RIT alone. Although there were increased deaths associated with the CMRIT method at the higher dose level, mortalities for the CMRIT method and RIT were not statistically different. These results indicate that significantly better outcome of therapy is associated with the CMRIT method compared to therapy with single agent, without an accompanied statistical increase in toxicity.

DeNardo et al. have reported that 250 μg cRGD pentapeptide (EMD 270179) provided 1 hour before RIT increased uptake of RIT by HBT 3477 tumors up to 50% (*Cancer Biother. Radiopharm.* 15: 71–79 (2000)). However, in a previous study of this HBT 3477 model using $^{90}$Y-DOTA-peptide-ChL6 at doses ranging from 110 μCi to 330 μCi increased cure rates did not follow increased injected doses above 260 μCi $^{90}$Y-DOTA-peptide-ChL6. These results strongly suggest that increased uptake of RIT associated with cRGD pentapeptide peptides such as cyclo-(Arg-Gly-Asp-D-Phe-[N-Me]-Val) is not the major factor responsible for the increased cures.

The vascular contribution to the CMRIT method was investigated by assessing endothelial apoptosis and its time course compared to tumor cell apoptosis. If cRGD pentapeptide induced endothelial apoptosis, and subsequently induced tumor cell apoptosis following the loss of endothelial cells, one would expect to observe increased endothelial apoptosis occurring prior to increased total cell apoptosis. A cRGD pentapeptide (cyclo-(Arg-Gly-Asp-D-Phe-[N-Me]-Val)) in combination with RIT (e.g., CMRIT method) elevated both endothelial and total cell apoptosis levels above that observed with RIT at almost all time points, with significantly increased levels at 1 and 5 days. In addition, a single dose of cyclo-(Arg-Gly-Asp-D-Phe-[N-Me]-Val) significantly increased endothelial apoptosis at the same time points compared to untreated. Although there was no clear pattern of endothelial apoptosis preceding total cell apoptosis, there was a persistent elevation of endothelial apoptosis in the CMRIT method compared to RIT. However, the effect of this difference was not reflected directly by differences in microvessel density at the time points assessed. It is possible that cyclo-(Arg-Gly-Asp-D-Phe-[N-Me]-Val) affected the quality of the microvascular organization, which would not have been reflected by the microvessel density. This is consistent with the decrease in proliferation observed at 6 days in the CMRIT method compared to RIT treated tumors, the latest time point evaluated, when the number of microvessels had decreased in both RIT and CMRIT method treated tumors.

Other possible differences between the CMRIT method and RIT could be related to indirect inhibitory effects of cRGD pentapeptides such as cyclo-(Arg-Gly-Asp-D-Phe-[N-Me]-Val). Radiation has been shown to induce the accumulation and activation of $\beta_3$ integrin on tumor blood vessels within 1–4 hours of irradiation. The increase is associated with platelet accumulation in the lumen of irradiated tumor vessels. Platelet adhesion to endothelial cells has been inhibited by blockade with antibody to $\alpha_v\beta_3$ integrin, and platelets potentially contribute to tumor angiogenesis through growth factors contained in α-granules. Cyclo-(Arg-Gly-Asp-D-Phe-[N-Me]-Val) has been reported to have an $IC_{50}$ of 420 nM for isolated $\alpha_{2b}\beta_3$ receptor, compared to 5 nM for $\alpha_v\beta_3$ It is possible that cyclo-(Arg-Gly-Asp-D-Phe-[N-Me]-Val), at this dose in this mouse model, inhibited accumulation of platelets in tumor vasculature in response to radiation, and thus decreased paracrine interaction to tumor cells. In addition, the $\alpha_v\beta_3$ integrin receptor has been reported to participate in the full activation of the vascular endothelial growth factor-2 (VEGFR-2)

receptor. In addition, inhibition by cRGD pentapeptides could interfere with downstream effects of the VEGFR-2 receptor on endothelial cells, such as decreased growth factor release to adjacent tumor cells, leading to overall inhibition of tumor cell proliferation.

The lack of responsiveness of HBT 3477 subcutaneous tumor growth to cyclo-(Arg-Gly-Asp-D-Phe-[N-Me]-Val) inhibition (single modality) likely indicates that in this model tumor growth utilizes existing blood vessels or that sufficient blood vessel growth occurs even in the presence of the cRGD pentapeptide. After RIT, at a time when blood vessel density has decreased substantially, cRGD pentapeptide inhibition may lead to decreased tumor cell and endothelial cell recovery from radiation damage, resulting in increased tumor cell death in waves of apoptosis, related to increased therapeutic efficacy.

The CMRIT method of the present invention provides increased efficacy of RIT for treatment of tumors resulting from combined treatment anti-angiogenic cyclic RGD pentapeptides. The therapeutic synergy observed for the CMRIT method of the present invention is likely due to the combined effects of several mechanisms, leading to increased apoptosis and decreased cell proliferation. The higher level of endothelial apoptosis observed with the CMRIT method would, however, be consistent with endothelial loss impacting tumor cell loss, and contributing to the observed increase in cures.

We claim:

1. A method of treating tumors in a patient comprising the sequential steps of:
   (a) administering to the patient at least one dose of an antiangiogenic cyclo-(arginine-glycine-aspartic acid)-containing pentapeptide (cRGD pentapeptide);
   (b) administering to the patient an anti-tumor effective amount of a radioimmunotherapeutic agent (RIT); and
   (c) thereafter administering to the patient at least one additional dose of cRGD pentapeptide.

2. The method of claim 1 wherein the cRGD pentapeptide is cyclo-(Arg-Gly-Asp-D-Phe-[N-Me]-Val).

3. The method of claim 1 wherein the cRGD pentapeptide dose in step (a) is administered no later than about one hour prior to the administration of the RIT.

4. The method of claim 1 wherein in step (c) a first additional dose of cRGD pentapeptide is administered within about two days after the administration of RIT.

5. The method of claim 1 wherein in step (c) at least 5 additional doses of cRGD pentapeptide are administered sequentially.

6. The method of claim 5 wherein each additional dose of cRGD pentapeptide is administered at intervals of no more than about two days between doses.

7. The method of claim 1 wherein the RIT is a radionuclide-labeled chelating agent-ligand complex in which chelating agent is chemically bonded to a tumor-targeting molecule.

8. The method of claim 7 wherein the tumor-targeting molecule is a monoclonal antibody.

9. The method of claim 8 wherein the monoclonal antibody is an anti-tumor monoclonal antibody.

10. The method of claim 9 wherein the anti-tumor monoclonal antibody is an anti-MUC-1 monoclonal antibody.

11. The method of claim 9 wherein the anti-tumor monoclonal antibody is a chimeric L6 monoclonal antibody.

12. The method of claim 9 wherein the anti-tumor monoclonal antibody is M170 anti-MUC-1 monoclonal antibody.

13. The method of claim 7 wherein the chelating agent is a polyazamacrocyclic group or a polyoxamacrocyclic group.

14. The method of claim 13 wherein said chelating group is derived from a member of the group consisting of:
   1,4,7,10-tetraazacyclododecane-N,N',N'',N'''-tetraacetic acid;
   1,4,7,10-tetraazacyclotridecane-N,N',N'',N'''-tetraacetic acid;
   1,4,8,11-tetraazacyclotetradecane-N,N',N'',N'''-tetraacetic acid; and
   1,5,9,13-tetraazacyclohexadecane-N,N',N'',N'''-tetraacetic acid.

15. The method of claim 7 wherein the radionuclide is $^{90}$Y.

16. The method of claim 7 wherein the chelating agent is N-substituted 1,4,7,10-tetraazacyclododecane-N,N',N'',N'''-tetraacetic acid; wherein the N-substituent is —CH$_2$C(=O)-(Gly)$_3$-L-(p-isothiocyanato)-Phe-amide and the radionuclide is $^{90}$Y.

17. The method of claim 1 wherein the tumor is a breast tumor.

18. A method of treating tumors in a patient comprising the sequential steps of:
   (a) administering to the patient at least one dose of cyclo-(Arg-Gly-Asp-D-Phe-[N-Me]-Val);
   (b) administering to the patient an anti-tumor effective amount of a radioimmunotherapeutic agent (RIT); and
   (c) thereafter administering to the patient at least one additional dose of cyclo-(Arg-Gly-Asp-D-Phe-[N-Me]-Val).

19. The method of claim 18 wherein the cyclo-(Arg-Gly-Asp-D-Phe-[N-Me]-Val) dose in step (a) is administered no later than about one hour prior to the administration of the RIT.

20. The method of claim 18 wherein in step (c) a first additional dose of cyclo-(Arg-Gly-Asp-D-Phe-[N-Me]-Val) is administered within about 2 days after the administration of RIT.

21. The method of claim 18 wherein in step (c) at least 5 additional doses of cyclo-(Arg-Gly-Asp-D-Phe-[N-Me]-Val) are administered sequentially.

22. The method of claim 21 wherein each additional dose of cyclo-(Arg-Gly-Asp-D-Phe-[N-Me]-Val) is administered intervals of no more than about two days between each dose.

23. The method of claim 18 wherein the RIT is a radionuclide-labeled chelating agent-ligand complex in which chelating agent is chemically bonded to a tumor-targeting molecule.

24. The method of claim 23 wherein the tumor-targeting molecule is a monoclonal antibody.

25. The method of claim 24 wherein the monoclonal antibody is a an anti-tumor monoclonal antibody.

26. The method of claim 25 wherein the anti-tumor monoclonal antibody is an anti-MUC-1 monoclonal antibody.

27. The method of claim 25 wherein the anti-tumor monoclonal antibody is a chimeric L6 monoclonal antibody.

28. The method of claim 25 wherein the anti-tumor monoclonal antibody is M170 anti-MUC-1 monoclonal antibody.

29. The method of claim 25 wherein the chelating agent is a polyazamacrocyclic group or a polyoxamacrocyclic group.

30. The method of claim 25 wherein said chelating agent is derived from a member of the group consisting of:
   1,4,7,10-tetraazacyclododecane-N,N',N'',N'''-tetraacetic acid;

1,4,7,10-tetraazacyclotridecane-N,N',N'',N'''-tetraacetic acid;

1,4,8,11-tetraazacyclotetradecane-N,N',N'',N'''-tetraacetic acid; and 1,5,9,13-tetraazacyclohexadecane-N,N',N'',N'''-tetraacetic acid.

31. The method of claim 25 wherein the radionuclide is $^{90}$Y.

32. The method of claim 25 wherein the chelating agent is N-substituted 1,4,7,10-tetraazacyclododecane-N,N',N'',N'''-tetraacetic acid; wherein the N-substituent is —CH$_2$C(═O)-(Gly)$_3$-L-(p-isothiocyanato)-Phe-amide and the radionuclide is $^{90}$Y.

33. The method of claim 18 wherein the tumor is a breast tumor.

* * * * *